United States Patent [19]

Petelenz et al.

[11] Patent Number: 5,087,242
[45] Date of Patent: Feb. 11, 1992

[54] HYDRATABLE BIOELECTRODE

[75] Inventors: Tomasz J. Petelenz; Stephen C. Jacobsen; Robert L. Stephen; Jon Beck, all of Salt Lake City, Utah; Jin Shimada, Falcon Heights, Minn.

[73] Assignee: Iomed, Inc., Salt Lake City, Utah

[21] Appl. No.: 383,939

[22] Filed: Jul. 21, 1989

[51] Int. Cl.$^5$ ............................................. A61N 1/30
[52] U.S. Cl. ................................... 604/20; 128/802
[58] Field of Search ............... 604/20, 891.1; 128/802, 128/803, 898; 424/447–449

[56] References Cited

U.S. PATENT DOCUMENTS

| | | | |
|---|---|---|---|
| 4,383,529 | 5/1983 | Webster | 128/802 |
| 4,416,274 | 11/1983 | Jacobsen et al. | 604/20 |
| 4,419,092 | 12/1983 | Jacobsen et al. | 128/803 |
| 4,474,570 | 10/1984 | Ariura et al. | 604/20 |
| 4,702,732 | 10/1987 | Powers et al. | 128/803 |
| 4,708,149 | 11/1987 | Axelgaard et al. | 128/802 |
| 4,731,926 | 3/1988 | Sibalis | 604/20 |
| 4,747,819 | 5/1988 | Phipps et al. | 604/20 |
| 4,921,475 | 5/1990 | Sibalis | 604/20 |

FOREIGN PATENT DOCUMENTS

| | | | |
|---|---|---|---|
| 0058920 | 9/1982 | European Pat. Off. | 604/20 |
| 0299615 | 1/1989 | European Pat. Off. | 604/20 |
| 2184016 | 6/1987 | United Kingdom | 604/20 |

Primary Examiner—C. Fred Rosenbaum
Assistant Examiner—Sharon Finkel
Attorney, Agent, or Firm—Hana Dolezalova

[57] ABSTRACT

A hydratable iontophoretic bioelectrode includes a layer of material for absorbing and holding an ionized fluid when placed in contact with the fluid. A conductive sheet of material is positioned in contact with one side of the layer of material and is connectable to an electrical charged source to receive a charge of the same polarity as the polarity of ions in the fluid. A support base holds the layer of material and conductive sheets in place to enable placement of the layer of material against the skin or tissue of a person into which ions from the ionized fluid are to be delivered. This is carried out by applying the charge in question to the conductive sheet to cause the ions in the layer of material to migrate therefrom into the person's skin or tissue.

6 Claims, 1 Drawing Sheet

HYDRATABLE BIOELECTRODE

BACKGROUND OF THE INVENTION

This invention relates to an iontophoretic bioelectrode system capable of absorbing an aqueous ionic solution for subsequent iontophoretic delivery into the skin or tissue of a patient.

Iontophoretic bioelectrodes, used in place of hypodermic needles to inject medications into a person's skin or tissue, typically include a pouch or similar enclosure formed with a wettable barrier or a microporous membrane on one side thereof See, for example, U.S. Pat. Nos. 4,250,878, 4,419,092 and 4,477,971. A medication solution containing ions to be delivered into the person's skin or tissue is injected into the pouch by means of a hypodermic needle, a syringe, etc. When the wettable barrier or membrane is placed against a person's skin and an electric current is supplied to the solution, the ions are caused to migrate from the solution, through the wettable barrier or membrane, and into the skin.

For the bioelectrodes described, barriers or membranes are required to retain the solution in the pouch while allowing ions to migrate therethrough. However, such barriers or membranes also inhibit wetting of the skin and thus the migration of ions to a certain extent, as compared to the situation if the solution were in direct contact with the skin.

Also, because of the use of a pouch or similar enclosure to contain the medication solution, a mechanism or structure on the enclosure is necessary for allowing the injection thereinto of the solution. Such structure has typically included some type of orifice containing a plug into which a hypodermic needle or syringe tube may be inserted to allow delivery of the solution through the orifice into the interior of the enclosure, while preventing the outflow of the solution after it has been injected into the enclosure. The requirement for such solution receiving mechanism on the enclosure, of course, increases the cost of the bioelectrode and gives rise to potential leakage locations.

SUMMARY OF THE INVENTION

It is an object of the invention to provide an inexpensive, skin contour conformable, and easy to construct iontophoretic bioelectrode.

It is an additional object of the invention to provide such an iontophoretic bioelectrode which allows for improved wetting of skin when placed in contact therewith, and efficient delivery of ions into the skin.

It is also an object of the invention to provide such an iontophoretic bioelectrode in which the need for special solution receiving structure or mechanisms is obviated.

It is a further object of the invention to provide such an iontophoretic bioelectrode capable of absorbing and holding an ion containing solution when placed in contact therewith.

The above and other objects of the invention are realized in a specific illustrative embodiment of a hydratable bioelectrode for delivering ions of an ionized fluid into a person's skin or tissue. The bioelectrode includes a layer of material for absorbing and holding the ionized fluid when placed in contact therewith, a conductive sheet disposed in close proximity to the layer of material for receiving an electrical charge of the same polarity as the polarity of ions in the fluid to thereby cause such ions to move from the layer of material away from the conductive sheet, and a support base on which the layer of material and conductive sheet are mounted.

In accordance with one aspect of the invention, the layer of material comprises a polymer (dehydrated hydrogel), either in a continuous, fibrous or granular form, suitably held in place by the support base. One arrangement for holding the polymer in place and for inhibiting the build-up of residue on the skin from the polymer involves the use of two layers of mesh material for holding the polymer therebetween. Exemplary hydratable polymers include at least partially dehydrated polyethylene oxide, at least partially dehydrated polyacrylamide, and ammonium polyacrylate.

In accordance with another aspect of the invention, the layer of hydratable material is composed of a matrix of fibers, such as cellulose fibers, impregnated or interwoven with a hydratable polymer.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
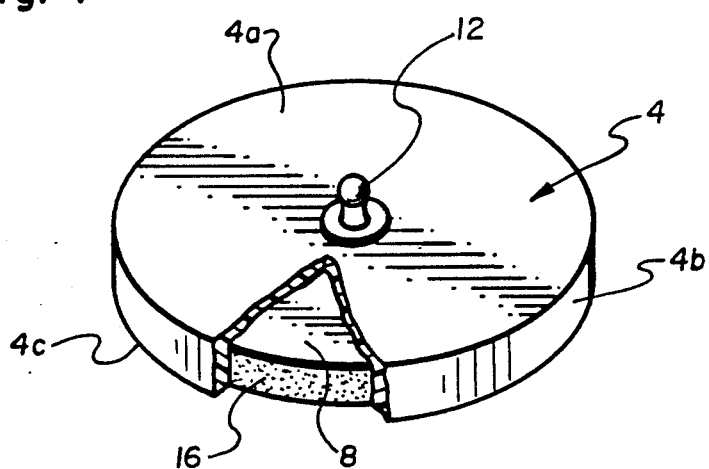
FIG. 1 is a perspective, partially cutaway view of an iontophoretic bioelectrode made in accordance with the principles of the present invention.
Figure 2:
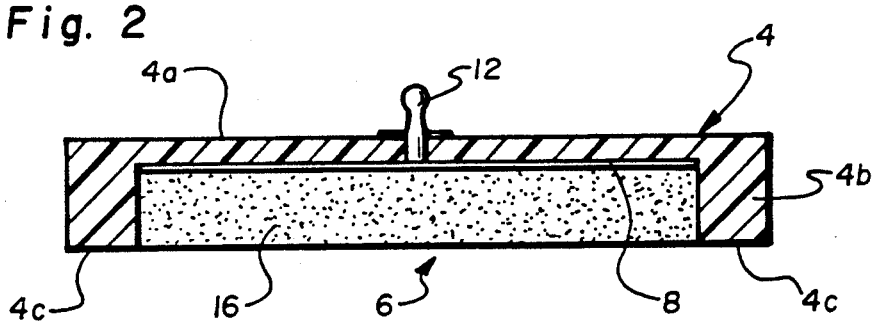
FIG. 2 is a side, cross-sectional view of the bioelectrode of FIG. 1.

Referring to FIGS. 1 and 2 there are shown a perspective, partially cut-away view and a side, cross-sectional view of an iontophoretic bioelectrode made in accordance with the present invention. The bioelectrode includes a generally circular support base or holder 4 made preferably of a flexible and electrically nonconductive material such as polyurethane, polyvinyl chloride or silicone. Alternatively, the support base 4 could be made to be substantially rigid. Although the support base is shown as being circular, it should be apparent that any shape or configuration suitable for carrying out the iontophoretic delivery of medication into a person would be suitable. The support base 4 of FIGS. 1 and 2 includes an upper, generally flat plate 4a and a skirt 4b projecting downwardly from the perimeter of the upper plate 4a to form a cavity 6 in the support base.

Disposed in the cavity 6 of the support base 4 immediately under the upper plate 4a is a circular electrically conductive sheet of material 8 for receiving an electrical charge of a predetermined polarity. The electrical charge is received via a conductive nipple 12 which extends from contact with the sheet of material 8 through the upper plate 4a of the support base 4, as shown in FIGS. 1 and 2. A conductive lead (not shown) for coupling an electrical charge source to the conductive sheet of material 8 may then be joined to the nipple 12 to carry the electrical charge to the conductive sheet. This, of course, is conventional and is shown in some of the patents earlier cited.

Also disposed in the cavity 6 of the support base 4 below the conductive sheet of material 8 is a hydratable layer of material 16. The hydratable material 16 and the conductive sheet of material 8 could be held in place within the support base 4 by a suitable adhesive preferably placed about the perimeter of the material 16. Advantageously, the conductive sheet of material 8 is in direct contact with the layer of hydratable material 16, and is generally coextensive therewith.

The hydratable layer 16 is composed of a material capable of absorbing and holding an ionized fluid when placed in contact therewith, which ionized fluid will be effectively retained until an electrical charge of the same polarity as the polarity of the ions contained in the fluid is supplied to the conductive sheet of material 8. Upon the application of such a charge, ions in the fluid contained in the layer of material 16 are caused to migrate away from the conductive sheet 8 and into the skin or tissue of a person over which the bioelectrode (and which is in contact with the hydratable layer 16). Of course, as described in the aforementioned patents, a second electrode for receiving an electrical charge of opposite polarity from that received by the bioelectrode of FIGS. 1 and 2 would be placed in contact with the skin or tissue in close proximity to the placement location of the bioelectrode. The use of two electrodes is conventional iontophoretic bioelectrode procedure. In this manner, the ionized medication is caused to migrate into the skin or tissue of the person being treated.

The hydratable layer 16 should be distinguished from materials such as sponge or fibrous masses which can absorb solutions and then discharge such solutions by mechanical means, e.g., squeezing. The solution absorbed by the hydratable layer 16 cannot be discharged by mechanical means.

The hydratable layer 16 is initially dehydrated or substantially dehydrated when disposed within the support base 4 and is thus in a reduced-volume condition. When placed in contact with the ionized fluid to be delivered into a patient, the hydratable layer 16 absorbs the fluid and expands to substantially fill the cavity 6 formed in the support base 4. (The bioelectrode may simply be immersed in the fluid to be absorbed or the bioelectrode could be turned over so that the hydratable layer 16 faces upwardly, and then the fluid could be poured, dripped or ejected onto the layer 16.) Advantageously, the hydratable layer 16 comprises a polymer such as polyethylene oxide, polyacrylamide, or ammonium polyacrylate. Such a polymer layer 16 assumes a tacky, adhesive characteristic when hydrated to adhere to skin with which it contacts.

Figure 3:
FIG. 3 is a side, cross-sectional view of one embodiment of the hydratable layer of the bioelectrode of FIG. 1.
Figure 4:
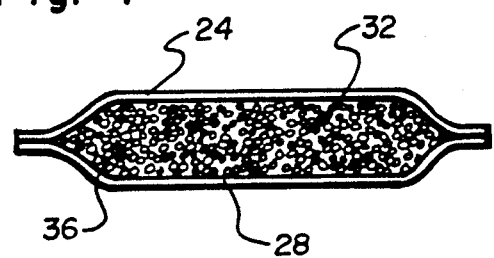
FIG. 4 is a side, cross-sectional view of another embodiment of the hydratable layer of the bioelectrode of FIG. 1.

The hydratable polymer layer 16 may take a variety of forms including that of a continuous polymer sheet, such as shown in FIG. 2, a fibrous polymer or another fibrous matrix impregnated with a hydratable polymer, such as shown in FIG. 3, and a granulated polymer held in place between two sheets of hydrophilic material such as shown in FIG. 4. The fibrous matrix, such as designated in FIG. 3 at 20, could be constructed of cellulose fibers wound and intertwined about one another and then impregnated with the polymer of interest; or the fibrous matrix could be composed simply of the polymer itself formed into strands suitable for intertwining and winding about one another.

FIG. 4 shows a side, cross-sectional view of a hydratable layer of material composed of two coextensive and spaced apart sheets of material 24 and 28 whose edges are joined together to define a cavity 32 between the sheets for holding the granulated polymer 36. The sheets of material 24 and 28 are permeable to liquids such as the ionic medications discussed herein. For example, the sheets of material 24 and 28 could be composed of a nylon mesh or a hydrophilic membrane such as polyurethane. The hydratable layer embodiment of FIG. 4 is not as effective in wetting of the skin as are the layers 16 and 20 of FIGS. 2 and 3 respectively and thus is not as effective in allowing the migration of ions from the hydratable polymer material to the skin.

As earlier indicated, it is desirable that the hydratable layer 16 assume a tacky, adhesive characteristic when hydrated, but if such a layer is not provided, then an adhesive could be applied externally to the bottom edges 4c of the support base 4 of FIGS. 1 and 2. Examples of such a tacky or sticky substance are polyacrylic acid and silicone pressure sensitive adhesive.

In tne manner described, an iontophoretic bioelectrode is provided in which the ionized medication may be absorbed into a hydratable layer in the bioelectrode upon contact between the layer and the medication. Thus, the need for specially designed solution receiving structure is avoided. In a preferred embodiment of the bioelectrode, a hydratable polymer is utilized which will absorb ionized medication and hold the medication until it is driven therefrom by the process of iontophoresis. Placing the polymer layer in direct contact with the skin or tissue of the person being treated allows for improved wetting of the skin or tissue and thus more efficient delivery of ions thereinto.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A hydratable bioelectrode for delivering ions of an ionized fluid into a person's skin or tissue comprising
    a layer of material for absorbing and holding the ionized fluid when placed in contact therewith,
    a conductive sheet disposed in close proximity to the layer of material for receiving an electrical charge of the same polarity as the polarity of ions in the fluid to thereby cause such ions form the layer of material away from the conductive sheet, and
    support means for holding the conductive sheet in close proximity to the layer of material,
    wherein said layer of material is comprised of a support matrix impregnated with the hydratable polymer, said support matrix comprising a nylon mesh.

2. A bioelectrode as in claim 1 wherein said polymer and matrix is granulated.

3. A bioelectrode as in claim 1 wherein said polymer and matrix is fibrous.

4. A hydratable bioelectrode for delivering ions of an ionized fluid into a person's skin or tissue comprising
    a layer of material for absorbing and holding the ionized fluid when placed in contact therewith,
    two coextensive sheets of material, at least one of the sheets comprising a conductive sheet, whose edges are formed together to define a cavity between the two sheets, at least one of said coextensive sheets being made of a hydrophilic material and at least one of the coextensive sheets being disposed in close proximity to the layer of material and at least one of the coextensive sheets being adapted for receiving an electrical charge of the same polarity as the polarity of ion sin the fluid to thereby cause such ions from the layer of material to move away from the conductive sheet, and support means for holding the conductive sheet in close proximity to the layer of material, wherein said layer of material is comprised of a support matrix impregnated with a granulated hydratable polymer.

5. A hydratable bioelectrode for delivering ions of an ionized fluid into a person's skin or tissue comprising a layer of material for absorbing and holding the ionized fluid when placed in contact therewith, two coextensive sheets of material, at least one of the sheets comprising a conductive sheet, whose edges are formed together to define a cavity between the two sheets, at least one of said coextensive sheets being made of a hydrophilic material and at least one of the coextensive sheets being disposed in close proximity to the layer of material and at least one of the coextensive sheets being adapted for receiving an electrical charge of the same polarity as the polarity of ions in the fluid to thereby cause such ions from the layer of material away from the conductive sheet, and support means for holding the conductive sheet in close proximity to the layer of material, wherein said layer of material is comprised of a support matrix impregnated with a fibrous hydratable polymer.

6. A bioelectrode as in claim 4 or 5 wherein said polymer is selected from the group consisting of polyacrylamide, polyacrylate, and cellulose.

* * * * *